(12) United States Patent
Yamamoto et al.

(10) Patent No.: US 8,849,374 B2
(45) Date of Patent: Sep. 30, 2014

(54) SURGERY ASSISTANCE SYSTEM AND OPTICAL AXIS POSITION MEASUREMENT DEVICE

(75) Inventors: Seiji Yamamoto, Shizuoka (JP); Toshihisa Takai, Shizuoka (JP); Etsukazu Hayashimoto, Shizuoka (JP); Masaaki Kinpara, Shizuoka (JP); Akira Miura, Shizuoka (JP)

(73) Assignee: National University Corporation Hamamatsu University School of Medicine, Shizuoka (JP)

( * ) Notice: Subject to any disclaimer, the term of this patent is extended or adjusted under 35 U.S.C. 154(b) by 1045 days.

(21) Appl. No.: 12/933,232

(22) PCT Filed: Mar. 17, 2009

(86) PCT No.: PCT/JP2009/055171
§ 371 (c)(1),
(2), (4) Date: Jan. 31, 2011

(87) PCT Pub. No.: WO2009/116535
PCT Pub. Date: Sep. 24, 2009

(65) Prior Publication Data
US 2011/0125006 A1 May 26, 2011

(30) Foreign Application Priority Data
Mar. 18, 2008 (JP) ................................. 2008-068606

(51) Int. Cl.
| | | |
|---|---|---|
| A61B 5/05 | (2006.01) | |
| A61B 19/00 | (2006.01) | |
| A61B 1/005 | (2006.01) | |
| A61B 5/103 | (2006.01) | |
| A61B 17/00 | (2006.01) | |
| A61B 5/06 | (2006.01) | |

(52) U.S. Cl.
CPC ... *A61B 19/5244* (2013.01); *A61B 2017/00725* (2013.01); *A61B 5/06* (2013.01); *A61B 1/0057* (2013.01); *A61B 2019/5255* (2013.01); *A61B 5/103* (2013.01); *A61B 2019/507* (2013.01)
USPC ........................................ 600/424

(58) Field of Classification Search
CPC ................. A61B 19/5244; A61B 2017/00725; A61B 2019/507; A61B 2019/5255; A61B 5/06; A61B 5/103
USPC ........................................ 600/427
See application file for complete search history.

(56) References Cited

U.S. PATENT DOCUMENTS

| | | | | |
|---|---|---|---|---|
| 7,161,741 | B1 * | 1/2007 | Schaack | 359/676 |
| 2005/0101855 | A1 * | 5/2005 | Miga et al. | 600/407 |
| 2006/0281971 | A1 * | 12/2006 | Sauer et al. | 600/109 |
| 2007/0142751 | A1 * | 6/2007 | Kang et al. | 600/587 |

FOREIGN PATENT DOCUMENTS

| | | |
|---|---|---|
| EP | 1982650 A1 | 10/2008 |
| JP | 2001-204738 A | 7/2001 |
| JP | 2001-293006 A | 10/2001 |
| JP | 2003-528688 T | 9/2003 |
| JP | 2007-209531 A | 8/2007 |
| WO | WO-01/74267 A1 | 10/2001 |

OTHER PUBLICATIONS

Shahidi et al. (Implementation, Calibration and Accuracy Testing of an Image-Enhanced Endoscopy System, IEEE Trans. on Medical Imaging, 21(12):1524-1535, 2002).*
Yamashita et al. (Real-Time 3-D Model-Based Navigation System for Endoscopic Paranasal Sinus Surgery. IEEE Trans. on Biomed. Eng., vol. 46, pp. 10-116, 1999).*

* cited by examiner

*Primary Examiner* — Jonathan Cwern
*Assistant Examiner* — Amelie R Gillman
(74) *Attorney, Agent, or Firm* — Rabin & Berdo, P.C.

(57) ABSTRACT

A surgery assistance system including a rigid endoscope having a position-orientation detection marker, 3-dimensional (3D) shape measurement device for obtaining data corresponding to a 3D surface of a patient and data corresponding to a 3D surface of the position-orientation detection marker, and computation unit for aligning pre-stored tomographical data of the patient and the data corresponding to the 3D surface of the patient, computing an optical axis of the rigid endoscope on the basis of the data corresponding to the 3D surface of the position-orientation detection marker and a pre-obtained 3D relative position relationship between an actual optical axis of the rigid endoscope and the position-orientation detection marker, for computing a tissue wall in the patient from the 3D tomographical data, and for computing an intersection of the tissue wall and the computed optical axis of the rigid endoscope.

16 Claims, 11 Drawing Sheets

SURGERY ASSISTANCE SYSTEM AND OPTICAL AXIS POSITION MEASUREMENT DEVICE

TECHNICAL FIELD

The present invention relates to a surgery assistance system for providing information relating to an image captured by a rigid endoscope to a surgeon or another user.

BACKGROUND ART

Surgical navigation (surgery assistance information display) has been performed in the past for displaying the proper position of the distal end of the surgical instrument on a CT (computed tomography) or MRI (magnetic resonance imaging) image to assist a surgeon when an endoscope or another surgical instrument is inserted into a patient's body. For example, Patent Document 1 describes a surgery assistance system proposed by the present inventors, which is a technique for aligning a 3-dimensional surface shape of a patient measured by a 3-dimensional shape measurement device with 3-dimensional tomographical data imaged in advance. A technique is also described whereby a 3-dimensional shape measurement device for measuring the 3-dimensional surface shape of a patient is used to measure an indicator part (sphere 12 in FIG. 1) for position and orientation detection that is attached to the surgical instrument, and the position and orientation of the surgical instrument is computed. However, these methods are merely for displaying the position of the distal end of a surgical instrument, pointer, or another instrument, and do not indicate the portion of a preoperative CT or MRI image to which a site imaged by an endoscope corresponds.

If it were possible to confirm the area of a preoperative CT or another image to which a site imaged by an endoscope (surgical area displayed on the monitor of an endoscope) corresponds, then, for example, a surgeon could freely take any surgical instrument in the right hand and continuously operate while using an endoscope held in the left hand to confirm the operated area by direct visual observation and recognize which area of a preoperative CT or another image is being observed.

Patent Documents 2 and 3 describe such conventional techniques whereby a site imaged by an endoscope is displayed on an image. Techniques proposed in the past by the present inventors include Japanese Patent Application No. 2007-22077 (not yet disclosed). Patent Document 2 describes a technique whereby the direction of the optical axis of a rigid endoscope in use is displayed on a 3-dimensional tomographic image in a surgery navigation device.

Patent Document 3 describes a technique whereby the location observed by an endoscope is determined and displayed on a preoperative CT/MRI through the use of an endoscope having distance measurement means (triangulation or ultrasonic sensor or the like using spotlight irradiation) for measuring the distance from the distal end of an insertion part of an endoscope inserted into a patient's body to an operation site within the patient's body.

In Patent Documents 2 and 3, a luminescent element or another marker and a position sensor for detecting the marker are used to detect the position and orientation of the endoscope, but these systems require that some type of marker be attached to the patient, or that a device be separately provided for measuring the shape of the patient in order to align the 3-dimensional tomographical data with a coordinate system for the patient, thus inconveniencing the patient and increasing the complexity of the system.

However, in the conventional technique of the present inventors described in Japanese Patent Application No. 2007-22077 (not yet disclosed), a 3-dimensional shape measurement device for measuring the 3-dimensional surface shape of the patient is used to detect the position and orientation of a rigid endoscope, and it is possible to prevent inconvenience to the patient and increased complexity of the system.

However, in Japanese Patent Application No. 2007-22077, the optical axis of the endoscope is assumed to be a nominal value, the same as in the techniques of Patent Documents 2 and 3, and calibration of the optical axis of the endoscope is not addressed. In a straight-view endoscope, for example, the optical axis information of the endoscope is displayed under the assumption that the optical axis of the endoscope passes through the center of the endoscope barrel, i.e., the optical axis has a nominal value such that the angle formed by the endoscope optical axis and a line through the center of the endoscope barrel is 0 degrees.

Since the objects viewed by an endoscope are usually relatively close to the lens, no consideration has been given to calibrating the optical axis of the endoscope, although calibration of lens position and other factors has been considered. In Patent Document 4, for example, a device is described for calibrating the lens position and field of view of an endoscope having a long shaft and a distal-end lens. However, the field of view of the endoscope is adjusted by displaying an existing image in the endoscope and adjusting the displayed image, and no description or suggestion is given of calibrating the optical axis of the endoscope.

[Patent Document 1] Publication of Unexamined Japanese Patent Application No. 2007-209531
[Patent Document 2] Publication of Unexamined Japanese Patent Application No. 2001-293006
[Patent Document 3] Publication of Unexamined Japanese Patent Application No. 2001-204738
[Patent Document 4] PCT (WO) 2003-528688

DISCLOSURE OF THE INVENTION

Problems to Be Solved by the Invention

Since the objects viewed by an endoscope are usually relatively close to the lens, misalignment of the actual optical axis from the nominal value rarely leads to significant effects, but in cases in which a straight line extended from the optical axis is displayed in order to navigate the movement of the endoscope, such as in a surgery assistance system, a difference between the actual optical axis (real optical axis) and the optical axis direction displayed in the navigation image becomes significant. The inventors have discovered that the misalignment of the actual optical axis from the nominal value is a value which cannot be ignored in developing a surgery assistance system. The inventors learned as a result of studying the optical axis positions of numerous endoscopes that in the case of an endoscope having a 120-degree angle of field, the misalignment of the actual optical axis from the nominal value is at most approximately 6 degrees (5% of the angle of field). Since surgery is a precision operation, an error of even a few millimeters can have adverse effects.

The present invention was developed to overcome the problems described above, and an object of the present invention is to provide a surgery assistance system for measuring an actual optical axis position of a rigid endoscope in advance and performing surgery navigation which takes into account the actual optical axis position even when the actual optical axis is offset from the nominal value.

Means for Solving the Problem

The present invention is configured as described below.

The present invention provides a surgery assistance system comprising 3-dimensional shape measurement means for measuring a 3-dimensional surface shape of a patient; a rigid endoscope to be inserted into the body of the patient; computation means; and display means; wherein the rigid endoscope has a position-orientation detection marker in a portion not inserted into the body, the position-orientation detection marker being measurable by the 3-dimensional shape measurement means;

3-dimensional tomographical data of the patient imaged in advance, and a 3-dimensional relative position relationship between the position-orientation detection marker and the real optical axis of the rigid endoscope measured in advance are stored in the computation means;

the computation means includes means for aligning the 3-dimensional tomographical data and the 3-dimensional surface shape of the patient measured by the 3-dimensional shape measurement means;

means for computing the position and orientation of the rigid endoscope on the basis of the position-orientation detection marker measured by the 3-dimensional shape measurement means;

means for computing the optical axis of the rigid endoscope on the basis of the position-orientation detection marker measured by the 3-dimensional shape measurement means and the 3-dimensional relative position relationship between the stored real optical axis of the rigid endoscope and the position-orientation detection marker;

means for computing a tissue wall in the patient from the 3-dimensional tomographical data; and intersection computation means for computing an intersection of the tissue wall and the real optical axis of the rigid endoscope; and the display means displays at least the aligned 3-dimensional tomographical data, the real optical axis of the rigid endoscope, and the intersection of the tissue wall and the real optical axis of the rigid endoscope.

The present invention also provides a surgery assistance system comprising 3-dimensional shape measurement means for measuring a 3-dimensional surface shape of a patient; a rigid endoscope to be inserted into the body of the patient; computation means; and display means; wherein the rigid endoscope has a position-orientation detection marker in a portion not inserted into the body, the position-orientation detection marker being measurable by the 3-dimensional shape measurement means;

3-dimensional tomographical data of the patient imaged in advance, and a 3-dimensional relative position relationship between the position-orientation detection marker and the real optical axis of the rigid endoscope measured in advance are stored in the computation means; the computation means includes means for aligning the 3-dimensional tomographical data and the 3-dimensional surface shape of the patient measured by the 3-dimensional shape measurement means;

means for computing the position and orientation of the rigid endoscope on the basis of the position-orientation detection marker measured by the 3-dimensional shape measurement means; and means for computing the real optical axis of the rigid endoscope on the basis of the position-orientation detection marker measured by the 3-dimensional shape measurement means and the 3-dimensional relative position relationship between the stored optical axis of the rigid endoscope and the position-orientation detection marker; and the display means displays at least the aligned 3-dimensional tomographical data and the real optical axis of the rigid endoscope.

The present invention also provides a surgery assistance method for computing an intersection of a tissue wall of a patient and the real optical axis of a rigid endoscope in a surgery assistance system comprising 3-dimensional shape measurement means for measuring a 3-dimensional surface shape of the patient; a rigid endoscope having a position-orientation detection marker measurable by the 3-dimensional shape measurement means; computation means; and display means; wherein 3-dimensional tomographical data of the patient imaged in advance, and a 3-dimensional relative position relationship between the real optical axis of the rigid endoscope measured in advance and the position-orientation detection marker are stored; and the surgery assistance method comprises a step of aligning the 3-dimensional tomographical data and the 3-dimensional surface shape of the patient measured by the 3-dimensional shape measurement means;

a step of computing the position and orientation of the rigid endoscope on the basis of the position-orientation detection marker measured by the 3-dimensional shape measurement means;

a step of computing the real optical axis of the rigid endoscope on the basis of the position-orientation detection marker measured by the 3-dimensional shape measurement means and the 3-dimensional relative position relationship between the stored real optical axis of the rigid endoscope and the position-orientation detection marker;

a step of computing a tissue wall in the patient from the 3-dimensional tomographical data;

an intersection computation step of computing an intersection of the tissue wall and the real optical axis of the rigid endoscope; and a step of displaying in the display means at least the aligned 3-dimensional tomographical data, the real optical axis of the rigid endoscope, and the intersection of the tissue wall and the real optical axis of the rigid endoscope.

The present invention also provides a surgery assistance program for computing an intersection of a tissue wall of a patient and the real optical axis of a rigid endoscope in a surgery assistance system comprising 3-dimensional shape measurement means for measuring a 3-dimensional surface shape of the patient; a rigid endoscope having a position-orientation detection marker measurable by the 3-dimensional shape measurement means; computation means; and display means; wherein 3-dimensional tomographical data of the patient imaged in advance, and a 3-dimensional relative position relationship between the real optical axis of the rigid endoscope measured in advance and the position-orientation detection marker are stored; and the surgery assistance program comprises a step of aligning the 3-dimensional tomographical data and the 3-dimensional surface shape of the patient measured by the 3-dimensional shape measurement means;

a step of computing the position and orientation of the rigid endoscope on the basis of the position-orientation detection marker measured by the 3-dimensional shape measurement means;

a step of computing the real optical axis of the rigid endoscope on the basis of the position-orientation detection marker measured by the 3-dimensional shape measurement means and the 3-dimensional relative position relationship between the stored real optical axis of the rigid endoscope and the position-orientation detection marker;

a step of computing a tissue wall in the patient from the 3-dimensional tomographical data;

an intersection computation step of computing an intersection of the tissue wall and the real optical axis of the rigid endoscope; and a step of displaying in the display means at least the aligned 3-dimensional tomographical data, the real optical axis of the rigid endoscope, and the intersection of the tissue wall and the real optical axis of the rigid endoscope.

The present invention has the preferred embodiments described below. The surgery assistance system further comprises an optical axis position measurement device used within the range of measurement of the 3-dimensional shape measurement means; the optical axis position measurement device has an optical axis position measurement marker measurable by the 3-dimensional shape measurement means; and the computation means computes and stores the 3-dimensional relative position relationship between the real optical axis of the rigid endoscope and the position-orientation detection marker on the basis of the position-orientation detection marker and the optical axis position measurement marker measured by the 3-dimensional shape measurement means The optical axis position measurement device has fixing means for fixing at least a distal end portion of the rigid endoscope; and a target in the optical axis direction of the rigid endoscope;

the optical axis position measurement marker is provided to each of the fixing means and the target;

the optical axis position measurement marker is measured by the 3-dimensional shape measurement means, whereby coordinates of the distal end of the rigid endoscope and coordinates of the target are measured; and the position of the real optical axis of the rigid endoscope is computed from the coordinates of the distal end of the rigid endoscope and the coordinates of the target.

The intersection computation means converts a tissue wall in the patient into polygon data and computes intersections of the real optical axis of the rigid endoscope with each surface constituting the polygon data.

The display means further displays an image captured by the rigid endoscope.

The method for measuring the real optical axis of the rigid endoscope has the preferred embodiments described below.

The surgery assistance system further comprises an optical axis position measurement device used within the range of measurement of the 3-dimensional shape measurement means;

the optical axis position measurement device has fixing means for fixing at least a distal end portion of the rigid endoscope; and a target in the optical axis direction of the rigid endoscope;

the optical axis position measurement marker is provided to each of the fixing means and the target, and the fixing means and the target are positioned apart from each other; and the surgery assistance method comprises a first position measurement step of bringing the distal end portion of the rigid endoscope into contact with a center of the target, and measuring the fixing means, the target, and the marker of the rigid endoscope through the use of the 3-dimensional shape measurement means to compute 3-dimensional coordinates of each of the fixing means, the target, and the marker of the rigid endoscope;

a step of separating the distal end portion of the rigid endoscope from the target and fixing the distal end portion to the fixing means, and moving the target so that the center of the field of view of the rigid endoscope coincides with the center of the target;

a second position measurement step of measuring the target and the marker of the rigid endoscope through the use of the 3-dimensional shape measurement means and computing 3-dimensional coordinates of each of the target and the marker of the rigid endoscope; and a step of computing the 3-dimensional relative positions of the real optical axis of the rigid endoscope and the position-orientation detection marker on the basis of the 3-dimensional coordinates of each of the fixing means, the target, and the marker of the rigid endoscope measured in the first position measurement step and the second position measurement step.

Effect of the Invention

The present invention is configured as described above, and is therefore capable of measuring an actual optical axis position of a rigid endoscope in advance and performing surgery navigation which takes into account the actual optical axis position even when the actual optical axis is offset from the nominal value (hereinafter, referred to as offset of the optical axis). Specifically, since data obtained by measuring the actual optical axis position are used rather than the conventional method of moving and adjusting the display image of the endoscope to adjust the offset of the optical axis, the optical axis of the rigid endoscope and the intersection of the optical axis with the body cavity can be displayed on a surgery navigation screen. The system is also simplified by using the 3-dimensional shape measurement device for measuring the 3-dimensional surface shape of the patient without modification to measure the actual optical axis position. Since the actual optical axis position can be measured immediately prior to surgery, even when the amount of misalignment of the optical axis changes with each surgical operation as repeated disinfections take place for use in surgery, using the data of the actual optical axis position obtained immediately prior to surgery enables surgery navigation to be made more precise.

Moreover, by measuring the exact position of the actual optical axis (real optical axis), it is possible to assist surgery by displaying the point at which the optical axis is centered on the endoscope screen (the true center of the observation screen), as well as displaying which region of the image of the navigation device (preoperative CT or another image) in which the true center of the observation screen is positioned.

BEST MODE FOR CARRYING OUT THE INVENTION

Figure 1:
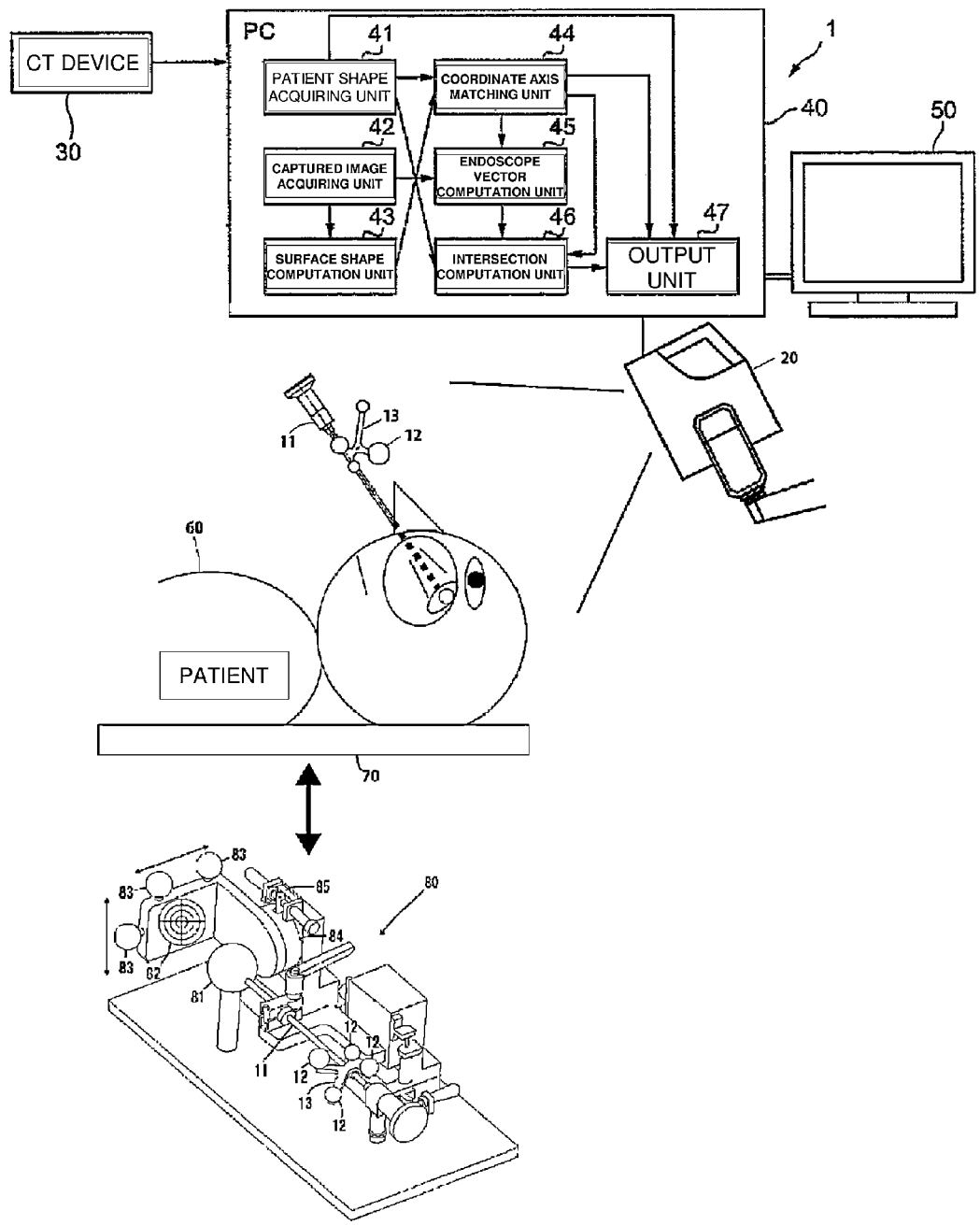
FIG. 1 is a view showing the configuration of the surgery assistance system according to an embodiment of the present invention.

Preferred embodiments of the surgery assistance system of the present invention will be described in detail with reference to the drawings. Reference symbols are used consistently to refer to the same elements in the drawings, and no redundant description thereof will be given. The embodiments described are also not necessarily shown to scale in the drawings.

FIG. 1 is a view showing the overall configuration of an embodiment of the surgery assistance system 1 of the present invention. The surgery assistance system 1 is a device for providing a surgeon or another user with information relating to an image captured by an endoscope during surgery on a patient 60. The surgery assistance system 1 according to the present embodiment is used for surgery that involves imaging by a rigid endoscope, such as endoscopic surgery on the paranasal sinus in otorhinolaryngology.

As shown in FIG. 1, the surgery assistance system 1 is composed of a rigid endoscope 11, ball markers 12, a 3-dimensional shape measurement device 20, a CT device 30, a PC (personal computer) 40, and a monitor 50. By placing an optical axis position measurement device 80 within the range of measurement of the 3-dimensional shape measurement device 20, a 3-dimensional relative position relationship can be measured between the ball markers 12 of the rigid endoscope 11 and the real optical axis. Measurement of the optical axis position will be described in detail hereinafter.

The rigid endoscope 11 is a device operated by a surgeon and inserted into the patient 60 to image the inside of the patient. The rigid endoscope 11 has a long, narrow shape to enable insertion into the body of the patient, and a mechanism for imaging the inside of the patient 60 is provided to the distal end portion of the rigid endoscope 11. This mechanism includes a lens provided in a position facing the imaged portion, and a CCD image sensor (charge coupled device image sensor) or another imaging element that is provided at the imaging position of the lens, for example. The imaging direction A of the rigid endoscope 11 is determined by the positioning of the mechanism described above. The imaging direction A of the rigid endoscope 11 is usually the optical axis direction of the lens. Information of an image captured by the rigid endoscope 11 is outputted to the PC 40 connected to the rigid endoscope 11 by a cable. There is no need for the rigid endoscope 11 described above to have a specialized structure; a conventional rigid endoscope can be used.

The ball markers 12 are objects capable of defining three or more fixed points fixedly provided at positions in a relative position relationship that is set in advance with respect to the imaging direction of the rigid endoscope 11. The ball markers 12 are scanned by the 3-dimensional shape measurement device 20, 3-dimensional coordinates of a plurality of points on the surface are calculated from the scan data, and the coordinates of the center of each ball are calculated from the sets of 3-dimensional coordinates calculated from the scan data. Specifically, the ball markers 12 are spherical members each having different sizes that are fixed to the rigid endoscope 11 via rod members 13. The ball markers 12 are formed in different sizes so that each ball is separately detected by calculating the diameter of each ball from the data scanned by the 3-dimensional shape measurement device 20.

The ball markers 12 are provided to the rigid endoscope 11 at a position behind the portion inserted into the patient 60, and are positioned at a portion of the rigid endoscope 11 not inserted into the patient 60. The portion of the rigid endoscope 11 extending from the portion inserted into the patient 60 to the portion to which the ball markers 12 are provided is formed from a rigid, non-bendable material so that a constant positional relationship is established between the ball markers 12 and the imaging direction A from the distal end portion of the rigid endoscope 11.

It is sufficient insofar as the objects capable of defining three or more fixed points provided to the rigid endoscope 11 are in positions in a constant relative position relationship to the imaging direction from the distal end portion of the rigid endoscope 11, and that the coordinates of three or more fixed points are calculated separately from the data scanned by the 3-dimensional shape measurement device 20. The objects are therefore not limited to being spheres such as the ball markers 12 of the present embodiment.

The 3-dimensional shape measurement device 20 is a device for 3-dimensionally scanning the ball markers 12 and the surface of the patient 60 when the rigid endoscope 11 is inserted into the patient 60. As shown in FIG. 1, in a case in which the rigid endoscope 11 is inserted from a nostril of the patient 60 and the head of the patient 60 is imaged by the rigid endoscope 11, the 3-dimensional shape measurement device 20 is provided in a position such that the ball markers 12 and the face of the patient 60 can be imaged. The 3-dimensional shape measurement device 20 is connected to the PC 40, and transmits scanned information to the PC 40.

The data scanned by the 3-dimensional shape measurement device 20 are used for computing 3-dimensional coordinates (3-dimensional position information) of a plurality of points on the surface of the scanned object. The phase shift device described in Japanese Laid-open Patent Publication No. 2003-254732, for example, can be used as the 3-dimensional shape measurement device 20. In this device, a grid pattern of white light similar to natural sunlight is projected from xenon lights, and a 3-dimensional scan is produced.

When an Fscan phase-shift 3-dimensional shape measurement device manufactured by Pulstec Industrial Co., Ltd. is used, an image can be captured from a distance of 90±10 cm in a measurement time of one second. The imaging resolution in this case is 0.1 to 0.6 mm. Specifically, a high-resolution color image having 3-dimensional position information can be acquired in one second. Since white light having a luminance approximately 28% of that of a cloudy day (outdoors) is used, and a laser or the like is not used, 3-dimensional position information of a human body can be safely acquired.

The CT device 30 acquires 3-dimensional tomographical data of the patient 60 into which the rigid endoscope 11 is inserted. The 3-dimensional tomographical data of the patient 60 acquired by the CT device 30 are data according to a first coordinate system.

The CT device 30 scans an object using radiation or the like and uses information indicating the 3-dimensional shape of the patient 60 to form an image (CT image) in which an internal structure processed using a computer is divided into circular cross-sections at equal intervals (1 mm, for example), and an existing CT device can be used as the CT device 30. The CT device 30 is connected to the PC 40, and transmits the acquired 3-dimensional tomographical data of the patient 60 to the PC 40. The CT device 30 also need not be placed at the same location as the 3-dimensional shape measurement device 20, and scanning by the 3-dimensional shape measurement device 20 and acquiring of 3-dimensional tomographical data by the CT device 30 are usually performed separately. The method described in Japanese Laid-open Patent Publication No. 2005-278992, for example, may be used to form the information indicating the 3-dimensional shape from the CT image.

In the surgery assistance system 1, since it is sufficient if information indicating a 3-dimensional shape that includes the inside of the patient 60 can be acquired, the means for acquiring the patient shape is not necessarily limited to the CT device 30, and an MRI device or ultrasound diagnostic device, for example, may be used.

The PC 40 is a device for receiving the data scanned by the 3-dimensional shape measurement device 20 and the 3-dimensional tomographical data of the patient 60 acquired by the CT device 30, and processing this data information. The PC 40 is composed specifically of a CPU (central processing unit), memory, and other hardware, and the functions of the PC 40 described below are realized by the operation of these information processing devices. As shown in FIG. 1, the PC 40 is provided with a patient shape acquiring unit 41, a captured image acquiring unit 42, a surface shape computation unit 43, a coordinate axis matching unit 44, an endoscope vector computation unit 45, an intersection computation unit 46, and an output unit 47 as functional constituent elements.

The patient shape acquiring unit 41 is means for receiving 3-dimensional tomographical data of the patient 60 which are transmitted from the CT device 30. The patient shape acquiring unit 41 outputs the received 3-dimensional tomographical data of the patient 60 to the coordinate axis matching unit 44, the intersection computation unit 46, and other components as needed. In the surgery assistance system 1, it is not necessarily required that the CT device 30 be provided as the patient shape acquiring means, as in the present embodiment; it is sufficient insofar as 3-dimensional tomographical data of the patient 60 (imaged or otherwise obtained by a CT device not included in the surgery assistance system 1) are received by the patient shape acquiring unit 41.

The captured image acquiring unit 42 is means for receiving the data scanned and transmitted by the 3-dimensional shape measurement device 20. The captured image acquiring unit 42 outputs the received data to the surface shape computation unit 43, the endoscope vector computation unit 45, and other components.

The surface shape computation unit 43 is surface shape computation means for computing a plurality of coordinate data representing the 3-dimensional shape of a surface of the patient 60 from the data scanned by the 3-dimensional shape measurement device 20. The surface of the patient 60 is the face of the patient 60 in the case of the present embodiment. The plurality of coordinate data representing the 3-dimensional shape acquired by the surface shape computation unit 43 are computed as coordinate data in a coordinate system set by the 3-dimensional shape measurement device 20, for example. This coordinate system differs from the first coordinate system mentioned above, and is a second coordinate system. Specifically, the plurality of coordinate data representing the 3-dimensional shape of the patient 60 according to the data scanned by the 3-dimensional shape measurement device 20 are data in a second coordinate system. The surface shape computation unit 43 outputs the computed data indicating the 3-dimensional shape of the surface of the patient 60 to the coordinate axis matching unit 44.

The coordinate axis matching unit 44 is a coordinate axis matching means for applying coordinate conversion to any one or both of the 3-dimensional tomographical data of the patient 60 acquired by the patient shape acquiring unit 41 and the data indicating the 3-dimensional shape of the surface of the patient 60 computed by the surface shape computation unit 43, and converting the data of the first coordinate system and the data of the second coordinate system into data having matching coordinate axes. Specifically, the coordinate axis matching unit 44 is means for enabling the 3-dimensional tomographical data of the CT device 30 and the data indicating the 3-dimensional shape computed from the data scanned by the 3-dimensional shape measurement device 20 to be processed as data of the same coordinate system.

Specifically, the coordinate axis matching unit 44 matches the coordinate axes by aligning the positions on the face of the patient 60 that are common to both the 3-dimensional tomographical data obtained by the CT device 30 and the data indicating the 3-dimensional shape that are computed from the data scanned by the 3-dimensional shape measurement device 20. The processing for matching the coordinate axes is accomplished through the use of a pattern matching method, for example, and as a result of this processing, a coordinate conversion function is computed for converting the coordinates of any one of the coordinate system data of the first coordinate system and the second coordinate system to the data of the other coordinate system. The coordinate axis matching unit 44 outputs the computed coordinate conversion function or the like to the endoscope vector computation unit 45, the intersection computation unit 46, the output unit 47, and other components as needed. After the processing described above for matching the coordinate axes, the coordinate conversion function or the like is applied to the data indicating the 3-dimensional shape in the endoscope vector computation unit 45, the intersection computation unit 46, the output unit 47, and other components, and the 3-dimensional tomographical data obtained by the CT device 30 and the data indicating the 3-dimensional shape computed from the data scanned by the 3-dimensional shape measurement device 20 are thereby processed in the same coordinate system.

The endoscope vector computation unit 45 is endoscope vector computation means for computing the central coordinates of the ball markers 12 from the plurality of coordinate data of the ball markers 12 scanned by the 3-dimensional shape measurement device 20, converting the coordinates through the use of the coordinate conversion function for producing data in accordance with the matched coordinate system computed by the coordinate axis matching unit 44, and computing the imaging direction vector A of the rigid endoscope 11 according to the matched coordinate system computed by the coordinate axis matching unit 44 from the coordinate-converted central coordinates of the ball markers 12 and the pre-stored position relationship between the centers of the ball markers 12 and the imaging direction from the distal end portion of the rigid endoscope 11. The position of the vector origin is included in the imaging direction vector A referred to herein. Specifically, the vector of the imaging direction A of the rigid endoscope 11 indicates from which direction and from which point an image is captured (that is, a 3D position of the image direction vetor A or a 3D position of the optical axis of the rigid endoscope 11). The endoscope vector computation unit 45 stores in advance information indicating the position relationship between the centers of the ball markers 12 and the imaging direction vector A of the rigid endoscope 11. Specific examples of the information indicating the position relationship include the coordinates of the distal end portion of the rigid endoscope 11, the coordinates of the target at which the optical axis (imaging direction vector A) of the rigid endoscope 11 coincides, and the central coordinates of the ball markers 12 in the same coordinate system. The endoscope vector computation unit 45 outputs the data of the computed imaging direction vector A to the intersection computation unit 46.

No problems occur when the optical axis (straight line indicating the imaging center in the imaging direction) of the rigid endoscope 11 is according to the nominal value declared by the manufacturer, but in actual practice, the optical axis is offset from the nominal value. For example, in the case of an endoscope having a 120-degree angle of field, the misalignment of the optical axis direction is at most approximately 6 degrees (5% of the angle of field). Consequently, when the imaging direction vector A is determined under the assumption that the optical axis is at the nominal value, inconsistency occurs between the actual field of view of the endoscope and the navigation information. The position relationship between the centers of the ball markers 12 and the imaging direction vector A of the rigid endoscope 11 stored in advance must therefore be based on measuring the actual optical axis position (imaging direction vector A) in the same coordinate system as the central coordinates of the ball markers 12.

Figure 2:
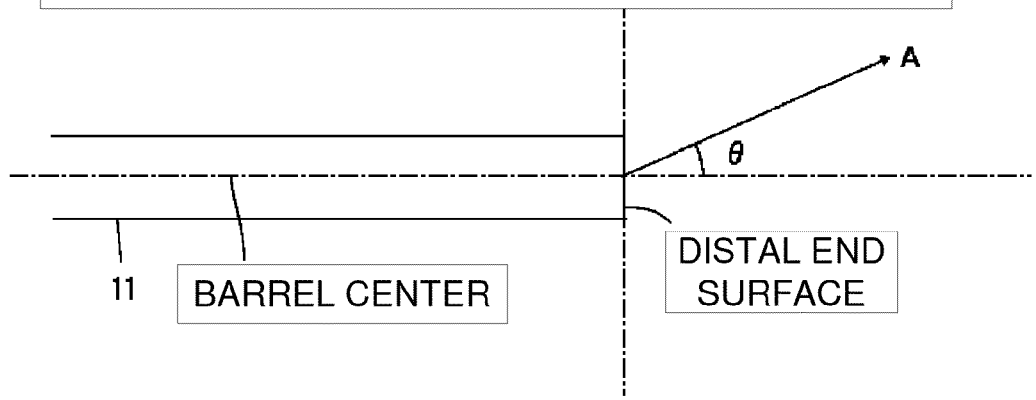
FIG. 2 is a view showing the offset of the optical axis of the rigid endoscope (straight-view endoscope)
Figure 2:
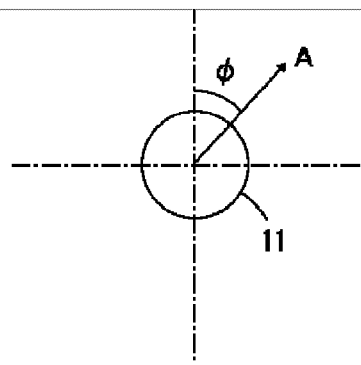
Figure 3:
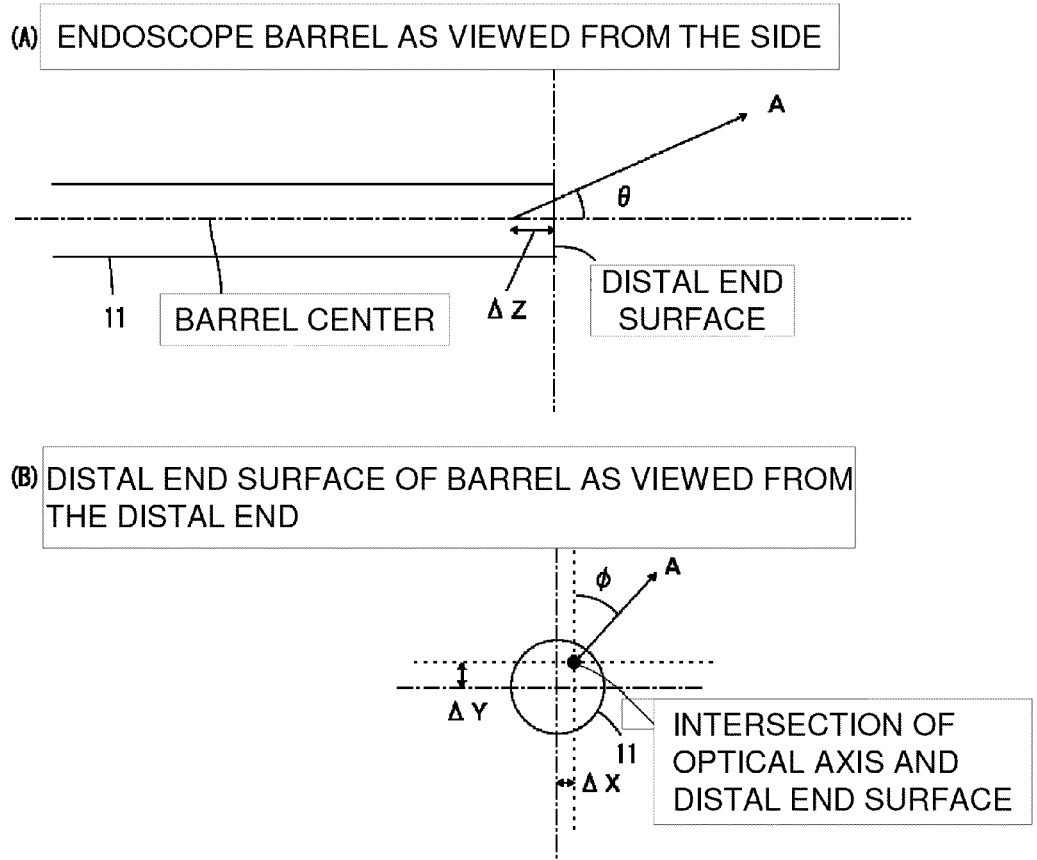
FIG. 3 is a view showing the offset of the optical axis of the rigid endoscope (straight-view endoscope)

An example of optical axis offset in a case in which the rigid endoscope 11 is a straight-view endoscope will be described using FIGS. 2 and 3. In a straight-view endoscope, the optical axis (straight line indicating the imaging center in the imaging direction) is expected to coincide with the center line of the endoscope barrel, but the optical axis is actually slightly offset for a variety of reasons. FIG. 2 shows an example in which an angle offset occurs at the distal end portion of the endoscope barrel due to the objective or another component. In the example shown in FIG. 2, the optical axis is offset θ degrees from the barrel center (FIG. 2(A)), and the direction of the offset is φ degrees from the zenith direction (FIG. 2(B)). In the example shown in FIG. 2, it is assumed that the optical axis offset occurs from the intersection of the distal end surface of the endoscope barrel and the barrel center, but the optical axis offset is not necessarily limited to occurring from this point. The offset can also begin closer to the eyepiece, as shown in FIG. 3(A), and the optical axis (straight line indicating the imaging center in the imaging direction) may sometimes not pass through the intersection of the distal end surface of the endoscope barrel and the barrel center, as shown in FIG. 3(B). The optical axis position may be measured by any method, but the optical axis position is preferably measured by the optical axis position measurement device described hereinafter as using the 3-dimensional shape measurement device 20. FIGS. 2 and 3 show examples using a straight-view endoscope, but it is apparent that the same optical axis offset can occur in an oblique-view endoscope or a side-view endoscope.

The intersection computation unit 46 is an intersection computation means for computing an intersection of the imaging direction vector A of the rigid endoscope 11 computed by the endoscope vector computation unit 45 and a surface constituting the inside of the patient 60 according to the information indicating the 3-dimensional shape acquired by the patient shape acquiring unit 41. This intersection is a point (center point) at which the rigid endoscope 11 captures an image in the information indicating the 3-dimensional shape obtained by the CT device 30. Specifically, the intersection computation unit 46 converts the surfaces constituting the inside of the patient 60 into polygon data and computes the coordinates of an intersection of the imaging direction vector A of the rigid endoscope 11 with each surface constituting the polygon data. Computation of the intersection coordinates will be described hereinafter in further detail. The intersection computation unit 46 outputs the data of the computed intersection coordinates to the output unit 47.

The output unit 47 is output means for superposing the data of the intersection coordinates computed by the intersection computation unit 46 onto the CT image data information indicating the surfaces constituting the inside of the patient 60 acquired by the patient shape acquiring unit 41, and outputting the superposed data to the monitor 50. The output unit 47 may also output to the monitor 50 the endoscope image data captured by the rigid endoscope 11 and inputted to the PC 40.

The monitor 50 displays information inputted from the PC 40. By referencing the monitor 50, the surgeon can know what portion of the inside of the patient 60 is being imaged by the rigid endoscope 11. The surgery assistance system 1 is configured as described above.

Figure 4:
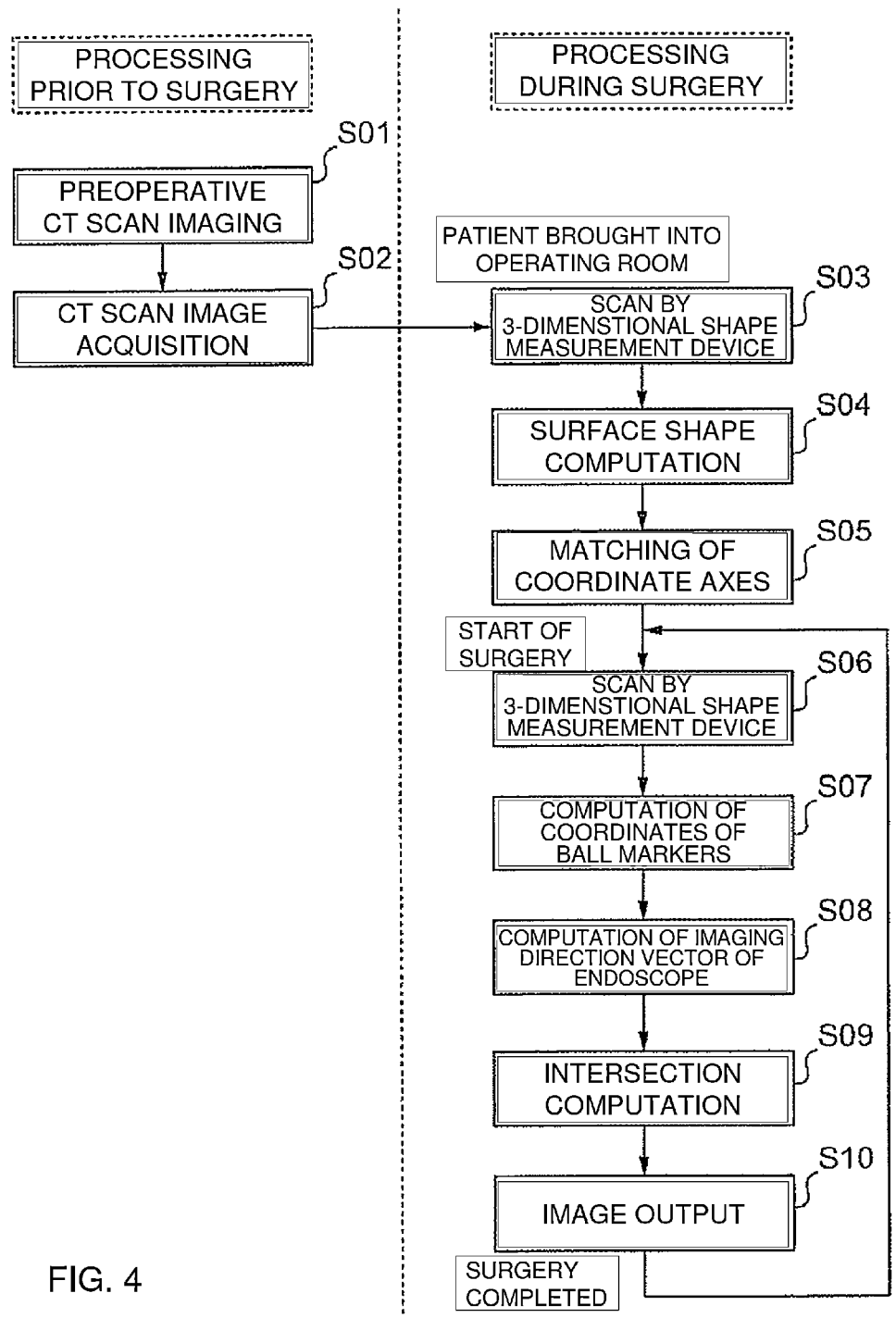
FIG. 4 is a flowchart showing the processing in the surgery assistance system according to an embodiment of the present invention.

The operation of the surgery assistance system 1 will next be described with reference to the flowchart of FIG. 4. This operation is performed when the rigid endoscope 11 is inserted for treatment or the like during surgery on the patient 60. The following description is of the process prior to surgery and the process during surgery.

First, prior to surgery, a CT scan image of the patient 60 is captured using the CT device 30 (S01). This CT scan imaging is of the site of the patient 60 at which the rigid endoscope 11 is inserted. Information is thereby acquired indicating the 3-dimensional shape of the face as the surface of the patient 60 and the surface constituting the inside of the patient 60 into which the rigid endoscope 11 is inserted. The information indicating the 3-dimensional shape of the patient 60 acquired by CT scan imaging by the CT device 30 is transmitted to the PC 40. The information is acquired by the patient shape acquiring unit 41 in the PC 40 and stored in the PC 40 (S02). The above operation is performed prior to surgery, e.g., at a time such as the day before surgery.

The process during surgery will next be described. The patient 60 is first brought into the operating room and placed face-up on an operating table 70 so that the rigid endoscope 11 can be inserted into a nostril. After the patient 60 is situated, the patient 60 is scanned by the 3-dimensional shape measurement device 20 before the rigid endoscope 11 is inserted (S03). The scan data are transmitted to the PC 40 from the 3-dimensional shape measurement device 20 and received by the captured image acquiring unit 42 in the PC 40. The received data are outputted from the captured image acquiring unit 42 to the surface shape computation unit 43.

In the surface shape computation unit 43, data indicating the 3-dimensional shape of the face as the surface of the patient 60 are computed from the data received by the surface shape computation unit 43 (S04). The computed data indicating the 3-dimensional shape of the face of the patient 60 are outputted from the surface shape computation unit 43 to the coordinate axis matching unit 44. At the same time, the data indicating the 3-dimensional shape of the patient 60 obtained by the CT device 30 and stored in the PC 40 are outputted from the patient shape acquiring unit 41 to the coordinate axis matching unit 44.

At this time, the coordinate axes of the respective coordinate systems are not the same in the data indicating the 3-dimensional shape of the patient 60 obtained by the CT device 30 and the data indicating the 3-dimensional shape of the face as the surface of the patient 60 computed from the data of the 3-dimensional shape measurement device 20. The data of the CT device 30 and the data of the 3-dimensional shape measurement device 20 are in a non-aligned state.

The shape of the face in the two sets of data are matched by the coordinate axis matching unit 44 to compute the coordinate conversion function, the data are subjected to coordinate conversion, and data are obtained in a coordinate axis in which the two sets of data are matched (S05). The shape of the face is matched by a pattern matching method such as described above. The entire face or the nose, cheeks, and other feature sites of the face are stored in advance as the sites to be matched. The coordinate conversion function for obtaining data having matching coordinate axes is outputted from the coordinate axis matching unit 44 to the endoscope vector computation unit 45, the intersection computation unit 46, and the output unit 47, the data are subjected to coordinate conversion or other processing, and information processing of the 3-dimensional shape is then performed based on the data having matching coordinate axes. The processing described above is performed by the time surgery is started.

The actual optical axis position of the rigid endoscope 11 is also measured and stored by the optical axis position measurement device described hereinafter prior to the start of surgery.

Surgery is then initiated, and the rigid endoscope 11 is inserted by the surgeon into the patient 60. The head of the patient 60 at this time has been kept immobile since the time that steps S03 through S05 were performed. This is to prevent misalignment of the coordinate axes. After the rigid endoscope 11 is inserted into the patient 60, the 3-dimensional shape measurement device 20 continues to scan the patient 60 and the ball markers 12 (S06). The scan data are transmitted from the 3-dimensional shape measurement device 20 to the PC 40 and received by the captured image acquiring unit 42 in the PC 40. The received data are outputted from the captured image acquiring unit 42 to the endoscope vector computation unit 45.

The 3-dimensional coordinates of the centers of the ball markers 12 are then computed by the endoscope vector computation unit 45 (S07). The imaging direction vector A of the rigid endoscope 11 is then computed as data in matched coordinate axes by the endoscope vector computation unit 45 from the computed 3-dimensional coordinates of the centers of the ball markers 12 on the basis of the position relationship between the central coordinates of the ball markers 12 and the imaging direction vector A of the rigid endoscope 11 stored in advance (S08). At this time, the imaging direction vector A of the rigid endoscope 11 is computed by using a position relationship between the central coordinates of the ball markers 12 and the actual optical axis position (imaging direction vector A) for each endoscope.

Information of the computed imaging direction vector A is outputted from the endoscope vector computation unit 45 to the intersection computation unit 46. At the same time, the information stored in the PC 40 indicating the 3-dimensional shape of the patient 60 obtained by the CT device 30 is outputted from the patient shape acquiring unit 41 to the intersection computation unit 46. An intersection of the imaging direction vector A of the endoscope 11 and a surface constituting the inside of the patient 60 is then computed by the intersection computation unit 46 (S09).

The intersection is computed as described below. First, the information indicating the 3-dimensional shape of the patient 60 obtained by the CT device 30 is converted into polygon data by the intersection computation unit 46. The conversion to polygon data may be performed prior to surgery and stored in the PC 40 in advance. Through this conversion, the surfaces constituting the (inside of the) patient 60 are made to form numerous triangles, for example. An intersection of the triangles and the imaging direction vector A of the rigid endoscope 11 is then computed.

Figure 5:
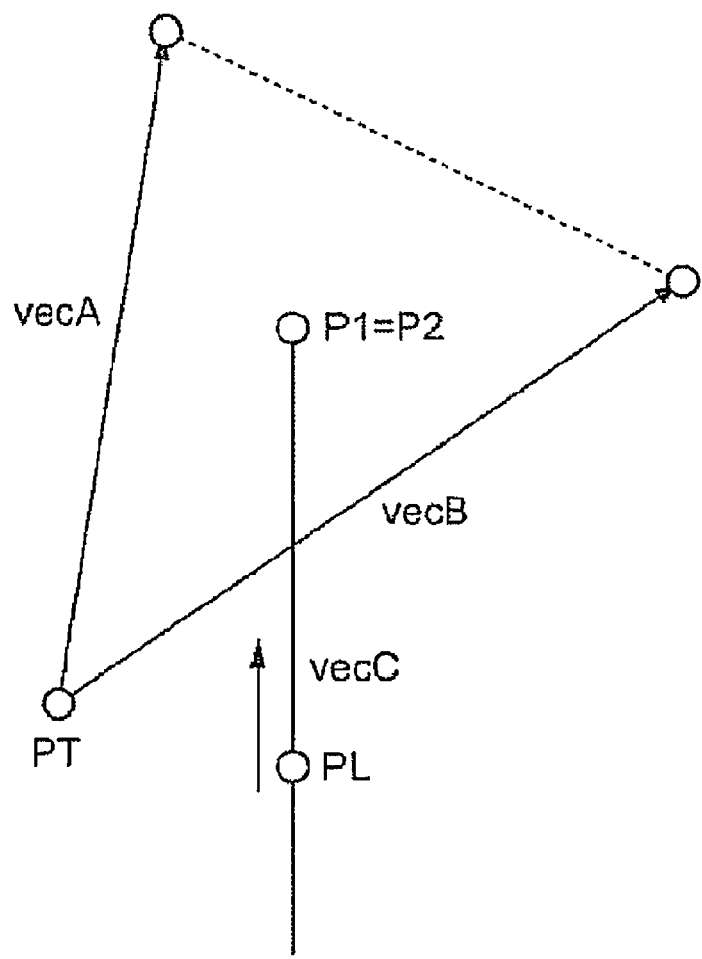
FIG. 5 is a view showing the intersection of a triangle forming a surface (tissue wall) of the patient and the vector of the imaging direction of the endoscope.

This computation of an intersection will be described using FIG. 5. The triangle can be expressed by the equation below, where PT is a reference point of the triangle constituting a polygon, vecA and vecB are the vectors of two sides of the triangle, and $\alpha$ and $\beta$ are two parameters.

$$P1 = PT + \alpha vecA + \beta vecB$$

The imaging direction A of the rigid endoscope 11 can be expressed by the equation below, where PL is a reference point (e.g., a point at the distal end of the rigid endoscope 11) for the imaging direction vector A of the rigid endoscope 11, vecC is a vector, and $\gamma$ is a parameter.

$$P2 = PL + \gamma vecC$$

When both equations intersect, then P1=P2. Under conditions in which the point such that P1=P2 exists within the triangle, the parameters satisfy the conditions below.

$0 < \alpha, 0 < \beta$ Condition 1

$0 < \alpha + \beta < 1$ Condition 2

$\gamma > 0$ Condition 3

The points that satisfy these conditions are derived for all of the triangles constituting the polygon data, and the distance between all of these points and the point at the distal end of the rigid endoscope 11 is calculated. The intersection at which this distance is shortest is the intersection of the imaging direction vector A of the rigid endoscope 11 and the surface constituting the inside of the patient 60.

Figure 6:
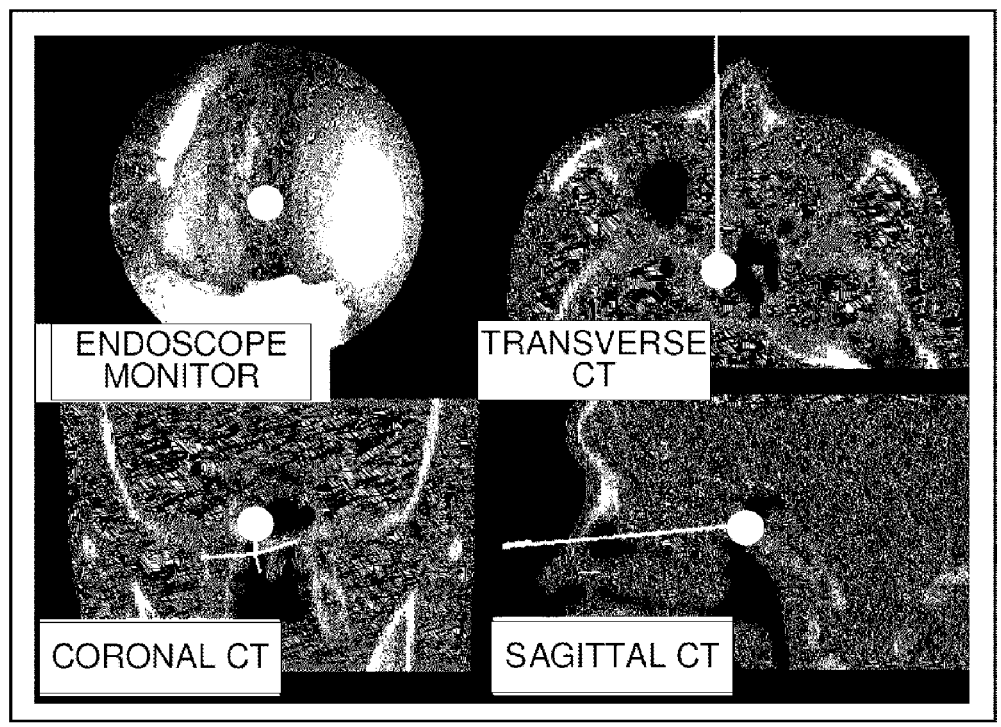
FIG. 6 is a view showing an example of the display of the intersection and the optical axis of the rigid endoscope.

Information of the coordinates of the computed intersection is outputted from the intersection computation unit 46 to the output unit 47. At this time, the CT image is outputted from the patient shape acquiring unit 41 to the output unit 47 as information indicating the surface constituting the inside of the patient 60. The information of the intersection is superposed by the output unit 47 on the location corresponding to the coordinates of the intersection on the CT image, which is the information indicating the surface constituting the inside of the patient 60, and inputted to the monitor 50. The inputted image is displayed by the monitor 50 (S10). The intersection information is displayed along with the optical axis of the rigid endoscope 11 on the 3-dimensional tomographical data and the image captured by the endoscope, as shown in FIG. 6, for example. By referencing the displayed image, the surgeon can know what portion of the inside of the patient 60 is being imaged by the rigid endoscope 11.

A configuration is preferably adopted in which the image captured by the rigid endoscope 11 is also received by the PC 40 and outputted to the monitor 50 from the output unit 47, and the location imaged by the rigid endoscope 11 is displayed along with a display indicating the position of the imaged portion.

The processing from S06 through S10 is repeated at regular intervals of one second, for example. The processing of S03 through S05 in the PC 40 differs from the processing of S06 through S10, but a configuration may be adopted in which the processing following S06 is performed automatically after the processing of S05 for matching the coordinate axes, for example. The surgeon or another user may also manually switch the processing.

Head movement by the patient 60 can also be allowed by repeating the processing of S03 through S10 at regular intervals after the initial alignment by the processing of S03 through S05. The processing of S03 through S05 may also be performed again for realignment when the head of the patient 60 is moved. Realignment may be performed by an operation of the surgeon or another user, for example, or may be triggered by comparing the aligned image with a subsequent image to detect head movement.

In the surgery assistance system 1 of the present embodiment as described above, information indicating the 3-dimensional shape of the surface of the patient and a surface constituting the inside of the patient 60 as imaged by the CT device 30, and data obtained by scanning the patient 60 from the outside using the 3-dimensional shape measurement device 20 can be used to display the site of the patient 60 to which a portion imaged by the rigid endoscope 11 corresponds. Consequently, the surgery assistance system 1 of the present embodiment enables the display described above to be produced without the use of a new specialized endoscope. Through the surgery assistance system 1 of the present embodiment, since the display described above is unaffected by such fluids as cerebrospinal fluid in the body of the patient, the display described above can be produced accurately. Use of the surgery assistance system 1 of the present embodiment therefore enables safe and precise surgery to be performed.

Convenience is further provided by the fact that there is no need of marking the patient 60 during CT scan imaging (S01), and the CT scan image can be captured in the usual manner. There is also no need to fix the patient 60 with pins or the like for alignment. Even if the patient 60 moves during surgery, alignment can easily be performed. The constituent elements of the surgery assistance system 1 described above are relatively inexpensive, and the present invention can be implemented at low cost.

Adopting a configuration in which the 3-dimensional information of the patient 60 obtained by the CT device 30 is converted to polygon data to calculate an intersection as in the present embodiment enables intersections to be reliably computed, and the present invention to be reliably implemented.

By adopting a configuration in which the image captured by the rigid endoscope 11 is displayed along with the information relating to the site of the patient 60 to which the portion imaged by the rigid endoscope 11 corresponds, the surgeon or the other user can simultaneously confirm both the details imaged by the rigid endoscope 11 and the information relating to the site of the patient 60 to which the portion imaged by the endoscope 11 corresponds. Surgery can therefore be assisted with greater convenience.

Figure 7:
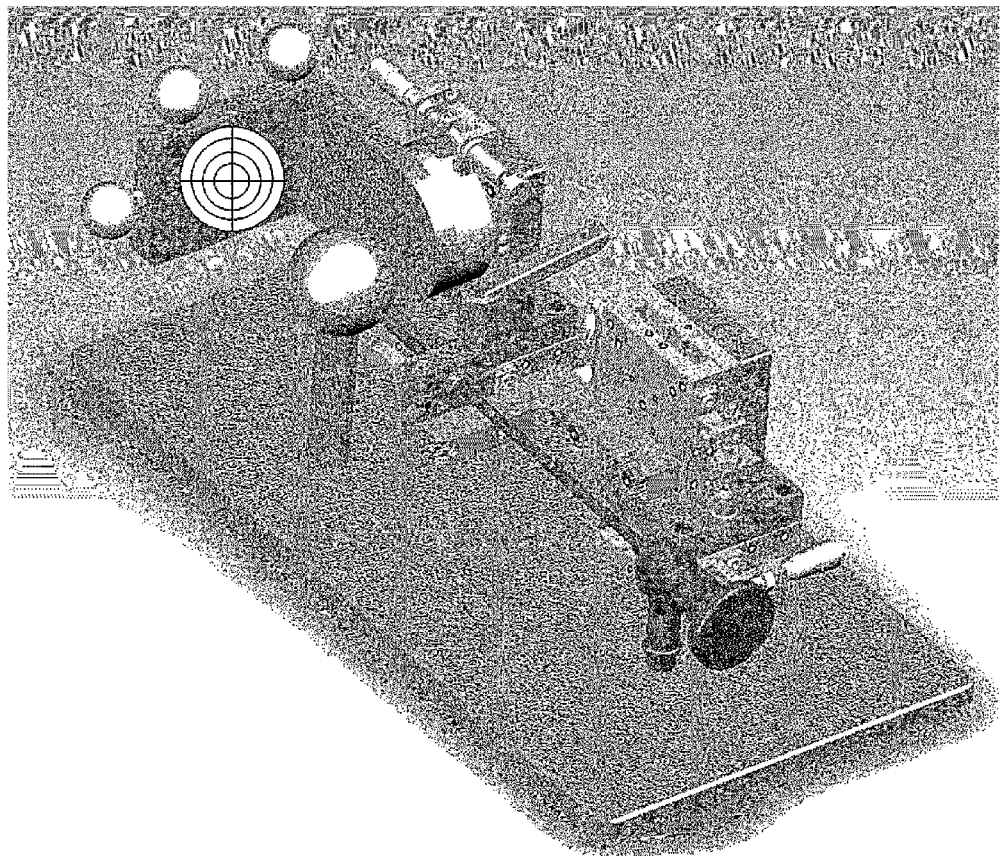
FIG. 7 is an image view showing the overall configuration of the optical axis position measurement device.
Figure 8:
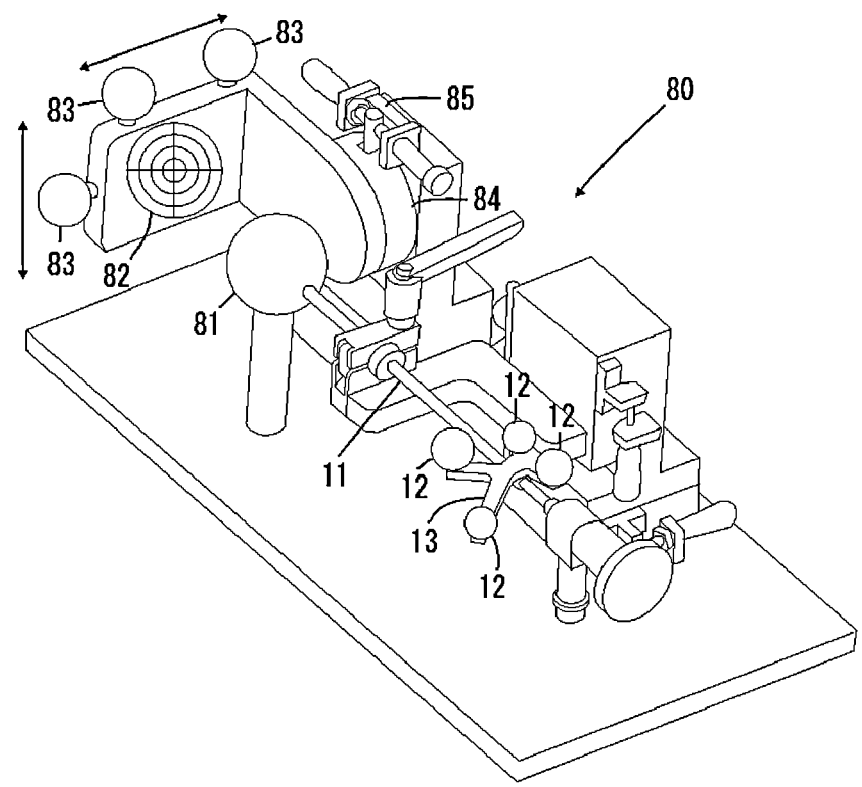
FIG. 8 is a schematic view showing the optical axis position measurement device of the rigid endoscope (straight-view endoscope)

The optical axis position measurement device will be described hereinafter using the drawings. FIG. 7 is a schematic view showing the optical axis position measurement device, and FIG. 8 is an outline view thereof. In FIG. 7, the ball markers 12 and the rod members 13 are omitted for convenience of view. The optical axis position measurement device 80 is composed of endoscope distal end fixing means 81 for fixing the distal end portion of the rigid endoscope 11; a target 82 for detecting a point observed by the rigid endoscope 11; target ball markers 83 (i.e., optical axis position measurement markers 83) attached to the target 82; and rotating means 84 for rotating the target 82 in a predetermined direction. In the present embodiment, the endoscope distal end fixing means 81 is spherical and also serves as a ball marker for measurement by the 3-dimensional shape measurement device 20. The rotating means 84 may be automated or manual.

A target movement means 85 is also provided. Adjusting the target movement means 85 enables the target 82 to be moved by minute amounts at least in two dimensions parallel to the target surface. As described hereinafter, alignment can be performed by using the target movement means 85 to move the target 82 during the process of placing the distal end portion of the rigid endoscope 11 and the center of the target in contact, and aligning the center of the field of view of the rigid endoscope 11 fixed to the endoscope distal end fixing means with the center of the target.

An example will next be described of the procedure whereby the optical axis position measurement device 80 is used to measure the optical axis position of the rigid endoscope 11.

(Step 1) The optical axis position measurement device 80 is placed within the range of measurement of the 3-dimensional shape measurement device 20.

(Step 2) The rigid endoscope 11, the position of the optical axis of which is to be measured, is set in the optical axis position measurement device 80.

Figure 11:
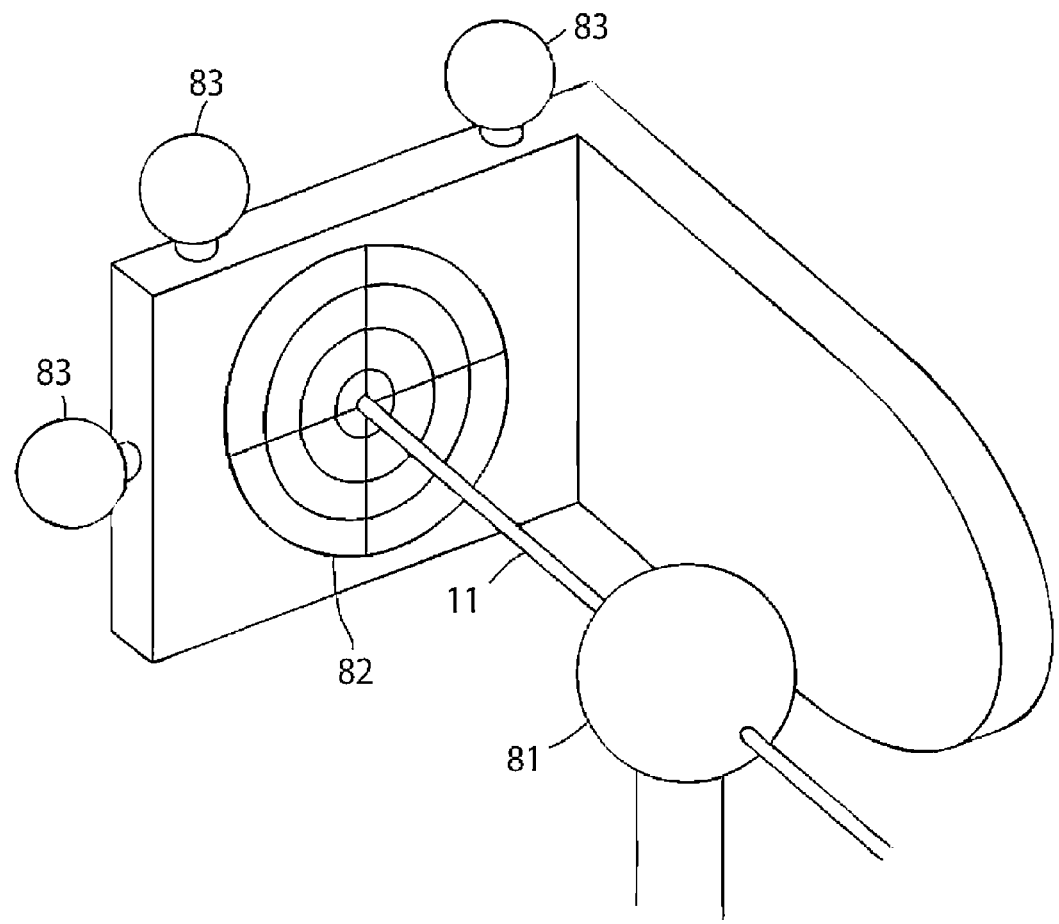
FIG. 11 is a view showing the distal end portion of the endoscope in contact with the center of the target.

(Step 3) The distal end portion of the rigid endoscope 11 is placed in contact with the target 82 and adjusted by the target movement means 85 so that the distal end portion of the rigid endoscope 11 and the center of the target 82 coincide. The barrel portion of the rigid endoscope 11 at this time is caused to pass through the endoscope distal end fixing means 81 (see FIG. 11). Once adjustment has been made by the target movement means 85 so that the distal end portion of the rigid endoscope 11 coincides with the center of the target 82, the rigid endoscope 11 is withdrawn without changing the position of the target 82, and the rigid endoscope 11 is fixed so that the distal end portion of the rigid endoscope 11 is positioned at the end of the endoscope distal end fixing means 81.

(Step 4) The target ball markers 83, the endoscope distal end fixing means 81, and the endoscope ball markers 12 are measured by the 3-dimensional shape measurement device 20, 3-dimensional shape data are extracted for each, and the data are processed to compute the central coordinates of the target 82, the central coordinates of the endoscope distal end fixing means 81, and the central coordinates of the ball markers 12.

(Step 5) Without moving the rigid endoscope 11 from the imaging position of step 4, the target 82 is moved by the target movement means 85 until the center of the field of view of the rigid endoscope 11 and the center of the target 82 coincide while the target 82 is observed from the eyepiece of the rigid endoscope 11.

(Step 6) The endoscope distal end fixing means 81, the target ball markers 83, and the ball markers 12 are measured using the 3-dimensional shape measurement device 20, 3-dimensional shape data are extracted for each, and the data are processed to compute the central coordinates of the target 82, the central coordinates of the endoscope distal end fixing means 81, and the central coordinates of the ball markers 12.

(Step 7) The 3-dimensional relative position relationship between the ball markers 12 and the optical axis position (real optical axis) of the rigid endoscope 11 is computed based on the central coordinates of the target 82 and central coordinates of the endoscope distal end fixing means 81 calculated in step 4, and the central coordinates of the ball markers 12, the central coordinates of the target 82, and the central coordinates of the endoscope distal end fixing means 81 calculated in step 7.

(Step 8) The computed 3-dimensional relative position relationship between the ball markers 12 and the optical axis position (including the coordinates of the distal end portion of the rigid endoscope 11) of the rigid endoscope 11 is stored in the PC 40.

The central coordinates of the target 82 are computed in steps 4 and 6 as described below. The central coordinates of the target 82 are calculated according to a separate coordinate system from the central coordinates of the target ball markers 83 and stored in advance in the PC 40. These central coordinates can be calculated by attaching a pin having a sphere at the head thereof perpendicular to the center of the target 82, measuring along with the target ball markers 83 through the use of the 3-dimensional shape measurement device 20, and processing the 3-dimensional shape data. Specifically, the central coordinates of each sphere and the plane expression for the surface of the target 82 are calculated by extracting each set of 3-dimensional shape data and processing the data, and the intersection coordinates are calculated as the central coordinates of the target 82 from the plane expression for the surface of the target 82 and the expression for the straight line computed from the central coordinates of the sphere at the head of the pin and the normal-line vector from the surface of the target 82. A coordinate conversion coefficient is then calculated from the central coordinates of the target ball markers 83 stored in advance and the central coordinates of the target ball markers 83 calculated by measurement by the 3-dimensional shape measurement device 20 and processing of the measurement data in steps 4 and 7, and the stored central coordinates of the target 82 are converted by the computed coordinate conversion coefficient. The central coordinates of the target 82 can thereby be calculated in the same coordinate system as the 3-dimensional shape data obtained by measurement by the 3-dimensional shape measurement device 20.

The 3-dimensional relationship between the ball markers 12 and the optical axis position (real optical axis) of the rigid endoscope 11 is computed in step 7 as described below. In a mechanism in which the central coordinates of the endoscope distal end fixing means 81 are the same as those of the distal end portion of the rigid endoscope 11, the computed central coordinates of the endoscope distal end fixing means 81 are the coordinates of the distal end portion of the rigid endoscope 11, and are also the coordinates of the origin of the imaging direction vector A. However, because such a mechanism is difficult to obtain, and the central coordinates of the endoscope distal end fixing means 81 and the coordinates of the distal end portion of the rigid endoscope 11 are sometimes offset from each other, the coordinates of the distal end portion of the rigid endoscope 11 can be computed from the size and direction of the offset. The size of the offset can easily be found by measuring the distance from the surface of the endoscope distal end fixing means 81 to the distal end portion of the rigid endoscope 11 when the rigid endoscope 11 is fixed to the endoscope distal end fixing means 81. This value is measured in advance and stored in the PC 40. The direction of the offset may be considered to be the vector that connects the central coordinates of the endoscope distal end fixing means 81 computed in step 4 and the central coordinates of the target 82. The direction of this vector is the direction of the offset. The component of the vector oriented toward the distal end portion of the rigid endoscope 11 from the central coordinates of the endoscope distal end fixing means 81 is computed from the direction of the vector and the stored size of the offset, and this vector component is added to the central coordinates of the endoscope distal end fixing means 81. The coordinates of the distal end portion of the rigid endoscope 11 are thereby computed.

The position vector connecting the computed coordinates of the distal end portion of the rigid endoscope 11 (coordinates of the origin of the imaging direction vector A) and the central coordinates of the target 82 computed in step 7 is the optical axis position (imaging direction vector A) of the rigid endoscope 11. To acquire this vector component and the origin coordinates of the vector, which are the coordinates of the distal end portion of the rigid endoscope 11, together with the central coordinates of the ball markers 12 is to acquire the 3-dimensional relationship between the ball markers 12 and the optical axis position of the rigid endoscope 11.

Figure 9:
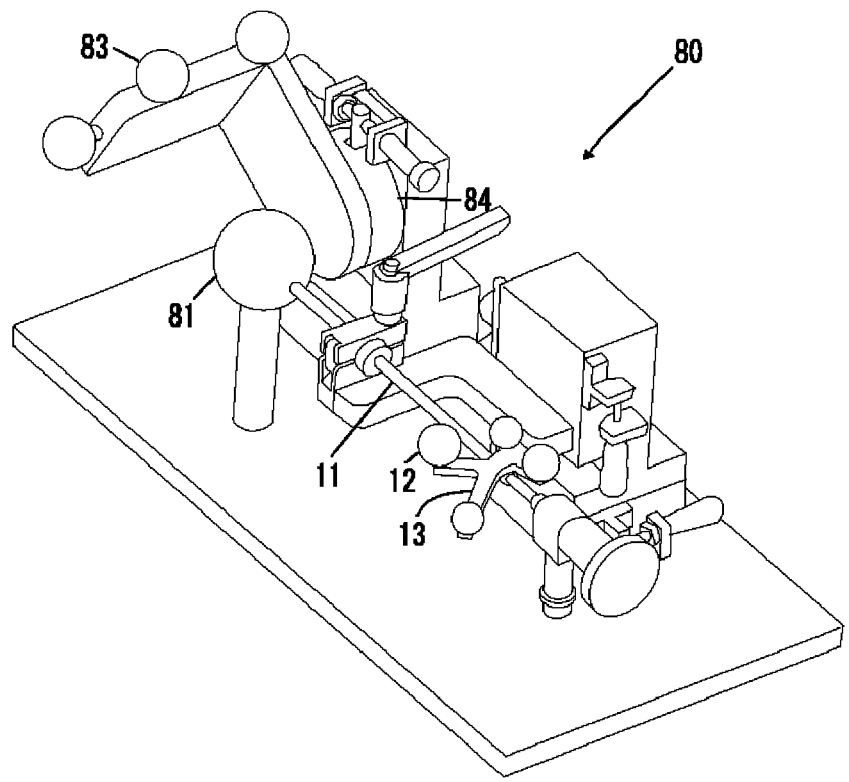
FIG. 9 is a schematic view showing the optical axis position measurement device of the rigid endoscope (30-degree oblique-viewing endoscope)
Figure 10:
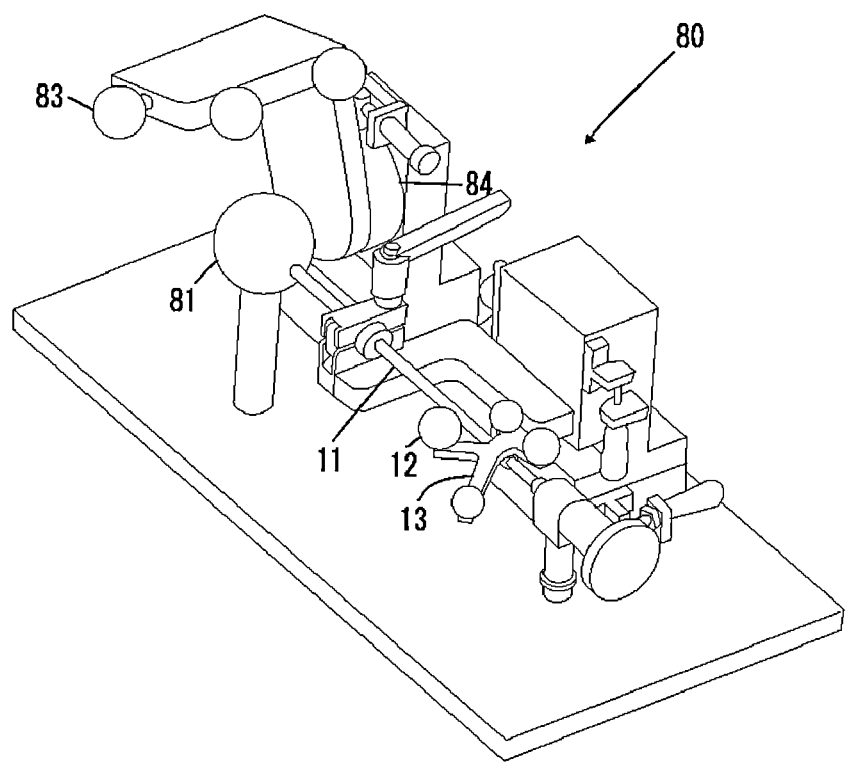
FIG. 10 is a schematic view showing the optical axis position measurement device of the rigid endoscope (70-degree oblique-viewing endoscope.

A case is described above in which the rigid endoscope 11 is a straight-view endoscope, but the optical axis position can be measured by the optical axis position measurement device 80 in the same manner in an oblique-view endoscope or a side-view endoscope. FIG. 9 shows an example of measuring the optical axis position in a 30-degree oblique view endoscope, and FIG. 10 shows an example of measuring the optical axis position in a 70-degree oblique view endoscope. As shown in these drawings, the rotating means 84 is rotated in accordance with the field of view direction (optical axis position) of the rigid endoscope 11 and adjusted so that the target 82 is within the field of view of the rigid endoscope 11. Even in the case of a side-view endoscope, the field of view of the rigid endoscope 11 can be maintained by placing the rigid endoscope 11 so that a portion of the objective at the distal end portion of the rigid endoscope 11 protrudes from the endoscope distal end fixing means 81, and the optical axis position of the rigid endoscope 11 can be measured without the endoscope distal end fixing means 81 obstructing the field of view.

The embodiment described above is an example in which the optical axis position can be measured when the optical axis is offset by the amounts corresponding to $\theta$ and $\phi$ in FIG. 2 by enabling the target 82 to move in two directions independently. It is also apparent that the optical axis position can be measured even when offset in dimensions corresponding to $\Delta X$, $\Delta Y$, and $\Delta Z$ as shown in FIG. 3 by adding such configurations as moving or rotating the barrel of the rigid endoscope 11, moving the endoscope distal end fixing means 81, or providing another target in front of the target 82 and on a transparent substrate capable of moving independently of the target 82, so as to provide more measurement points or acquire more measurement data. Examples of these specific configurations are not described, but these configurations can be implemented by one having ordinary skill in the art, and are thus included in the scope of the present invention.

An example of an embodiment of the present invention was described above, but the present invention is not limited by this example; various modifications thereof are possible within the category of the technical idea described by the claims.

[Key to Symbols]

1: surgery assistance system, 11: rigid endoscope, 12: ball markers, 20: 3-dimensional shape measurement device, 30: CT device, 40: PC, 41: patient shape acquiring unit, 42: captured image acquiring unit, 43: surface shape computation unit, 44: coordinate axis matching unit, 45: endoscope vector computation unit, 46: intersection computation unit, 47: output unit, 50: monitor, 60: patient, 70: operating table, 80: optical axis position measurement device, 81: endoscope distal end fixing means, 82: target, 83: target ball markers, 84: rotating means, 85: target movement means

The invention claimed is:

1. A surgery assistance system, comprising:
a rigid endoscope having a position-orientation detection marker;
3-dimensional (3D) shape measurement means for obtaining data corresponding to a 3D surface of a patient, and data corresponding to a 3D surface of the position-orientation detection marker;
computation means including
means for aligning pre-stored tomographical data of the patient and the data corresponding to the 3D surface of said patient measured by said 3D shape measurement means;
means for computing a 3D position of an optical axis of said rigid endoscope on the basis of first data corresponding to the 3D surface of said position-orientation detection marker measured by said 3D shape measurement means after the rigid endoscope is inserted into the patient and a pre-obtained 3D relative position relationship between an actual optical axis of said rigid endoscope and said position-orientation detection marker;
means for identifying a tissue wall in the patient from said 3D tomographical data; and
intersection computation means for computing an intersection of said tissue wall and the optical axis of said rigid endoscope of which the 3D position is computed; and
display means for displaying said 3D tomographical data, the optical axis of said rigid endoscope of which the 3D position is computed, and the intersection of said tissue wall and the optical axis of said rigid endoscope of which the 3D position is computed.

2. The surgery assistance system according to claim 1, further comprising:
an optical axis position measurement device including an optical axis position measurement marker, wherein
the 3D shape measurement means is configured to obtain data corresponding to a 3D surface of the optical axis position measurement marker; and
said computation means is configured to compute a 3D relative position relationship between the actual optical axis of said rigid endoscope and said position-orientation detection marker on the basis of second data corresponding to the 3D surface of said position-orientation detection marker measured by the 3D shape measurement means before the rigid endoscope is inserted into the patient and the data corresponding to the 3D surface of said optical axis position measurement marker, and to use the 3D relative position relationship as the pre-obtained 3D relative position relationship.

3. The surgery assistance system according to claim 2, wherein
said optical axis position measurement device includes fixing means for fixing a distal end portion of said rigid endoscope, and a target; and
the computing means is configured to obtain coordinates of the distal end portion of said rigid endoscope and coordinates of said target using the data corresponding to the 3D surface of said optical axis position measurement marker, and to compute a 3D position of the actual optical axis of said rigid endoscope from the coordinates of the distal end portion of said rigid endoscope and the coordinates of said target.

4. The surgery assistance system according to claim 3, wherein said intersection computation means is configured to convert a data representation of the tissue wall in said patient into a data representation of a polygon, and to compute intersections of the optical axis of said rigid endoscope of which the 3D position is computed with surfaces of said polygon as the intersection of said tissue wall and the optical axis of which the 3D position is computed.

5. The surgery assistance system according to claim 4, wherein said display means is configured to further display an image captured by said rigid endoscope.

6. The surgery assistance system according to claim 3, wherein said display means is configured to further display an image captured by said rigid endoscope.

7. The surgery assistance system according to claim 2, wherein said intersection computation means is configured to convert a data representation of the tissue wall in said patient into a data representation of a polygon, and to compute intersections of the optical axis of said rigid endoscope of which the 3D position is computed with surfaces of said polygon as the intersection of said tissue wall and the optical axis of which the 3D position is computed.

8. The surgery assistance system according to claim 7, wherein said display means is configured to further display an image captured by said rigid endoscope.

9. The surgery assistance system according to claim 2, wherein said display means is configured to further display an image captured by said rigid endoscope.

10. The surgery assistance system according to claim 1, wherein said intersection computation means is configured to convert a data representation of the tissue wall in said patient into a data representation of a polygon, and to compute intersections of the optical axis of said rigid endoscope of which the 3D position is computed with surfaces of said polygon as the intersection of said tissue wall and the optical axis of which the 3D position is computed.

11. The surgery assistance system according to claim 10, wherein said display means is configured to further display an image captured by said rigid endoscope.

12. The surgery assistance system according to claim 1, wherein said display means is configured to further display an image captured by said rigid endoscope.

13. A surgery assistance system, comprising:
a rigid endoscope having a position-orientation detection marker;
3-dimensional (3D) shape measurement means for obtaining data corresponding to a 3D surface of a patient and data corresponding to a 3D surface of the position-orientation detection marker;
computation means including
means for aligning pre-stored tomographical data of the patient and the data corresponding to the 3D surface of said patient measured by said 3D shape measurement means;
means for computing a 3D position of an optical axis of said rigid endoscope on the basis of the data corresponding to the 3D surface of said position-orientation detection marker measured by said 3D shape measurement means after the rigid endoscope is inserted into the patient and a pre-obtained 3D relative position relationship between an actual optical axis of said rigid endoscope and said position-orientation detection marker; and
display means for displaying said 3D tomographical data and the optical axis of said rigid endoscope of which the 3D position is computed.

14. A surgery assistance method for a surgery assistance system including 3-dimensional (3D) shape measurement means, a rigid endoscope having a position-orientation detection marker, computation means and display means, the method comprising:

receiving 3D tomographical data of said patient, and obtaining a 3D relative position relationship between an actual optical axis of said rigid endoscope and said position-orientation detection marker;

obtaining, using the 3D shape measurement means, data corresponding to the 3D surface of a patient before the rigid endoscope is inserted into the patient;

aligning, by the computing means, said 3D tomographical data and the data corresponding to the 3D surface of said patient; and obtaining, using the 3D shape measurement means, data corresponding to the 3D surface of said position-orientation detection marker after the rigid endoscope is inserted into the patient;

computing, by the computing means, a 3D position of an optical axis of said rigid endoscope on the basis of the obtained data corresponding to the 3D surface of said position-orientation detection marker and the 3D relative position relationship between said actual optical axis of said rigid endoscope and said position-orientation detection marker;

identifying, by the computing means, a tissue wall in the patient from said 3D tomographical data;

computing, by the computing means, an intersection of said tissue wall and the optical axis of said rigid endoscope of which the 3D position is computed; and displaying, by the display means, said 3D tomographical data, the optical axis of said rigid endoscope of which the 3D position is computed, and the intersection of said tissue wall and the optical axis of said rigid endoscope of which the 3D position is computed.

15. The surgery assistance method according to claim 14, wherein said surgery assistance system further comprises an optical axis position measurement device including fixing means for fixing a distal end portion of said rigid endoscope, and a target said fixing means and said target being positioned apart from each other; and said surgery assistance method comprises, before the rigid endoscope is inserted into the patient, a first position measurement step of bringing the distal end portion of said rigid endoscope into contact with a center of said target, measuring said fixing means, said target, and the position-orientation detection marker of said rigid endoscope using said 3D shape measurement means, and computing 3D coordinates of each of said fixing means, said target, and the position-orientation detection marker of said rigid endoscope;

a step of separating the distal end portion of said rigid endoscope from said target and fixing the distal end portion to said fixing means, and moving said target so that the center of the field of view of said rigid endoscope coincides with the center of said target;

a second position measurement step of measuring said target and the position-orientation detection marker of said rigid endoscope using said 3D shape measurement means and computing 3D coordinates of each of said target and the position-orientation detection marker of said rigid endoscope; and a step of computing and storing the 3D relative relationship of the actual optical axis of said rigid endoscope and said position-orientation detection marker on the basis of the 3D coordinates of each of said fixing means, said target, and the position-orientation detection marker of said rigid endoscope measured in said first position measurement step and said second position measurement step.

16. A non-transitory computer readable medium containing program instructions for a surgery assistance method in a surgery assistance system including a rigid endoscope having a position-orientation detection marker, and 3-dimensional (3D) shape measurement means for obtaining data corresponding to a 3D surface of a patient and data corresponding to a 3D surface of the position-orientation detection marker, execution of the program instructions causing one or more computer processors to perform the steps of:

receiving 3D tomographical data of said patient, and obtaining a 3D relative position relationship between an actual optical axis of said rigid endoscope and said position-orientation detection marker;

obtaining the data corresponding to the 3D surface of the patient measured by the 3D shape measurement means;

aligning said 3D tomographical data and the obtained data corresponding to the 3D surface of said patient;

obtaining the data corresponding to the 3D surface of said position-orientation detection marker measured by the 3D shape measurement means after the rigid endoscope is inserted into the patient;

computing a 3D position of an optical axis of said rigid endoscope on the basis of the obtained data corresponding to the 3D surface of said position-orientation detection and the 3D relative position relationship between said actual optical axis of said rigid endoscope and said position-orientation detection marker;

identifying a tissue wall in the patient from said 3D tomographical data;

computing an intersection of said tissue wall and the optical axis of said rigid endoscope of which the 3D position is computed; and causing display means to display said 3D tomographical data, the optical axis of said rigid endoscope of which the 3Dposition is computed, and the intersection of said tissue wall and the optical axis of said rigid endoscope of which the 3D position is computed.

* * * * *